US006153426A

United States Patent [19]

Heimberg

[11] Patent Number: 6,153,426

[45] Date of Patent: Nov. 28, 2000

[54] THERMOCYCLER APPARATUS

[75] Inventor: Wolfgang Heimberg, Ebersberg, Germany

[73] Assignee: MWG Biotech AG, Ebersberg, Germany

[21] Appl. No.: 09/467,322

[22] Filed: Dec. 20, 1999

[30] Foreign Application Priority Data

Dec. 22, 1998 [DE] Germany .......................... 198 59 586

[51] Int. Cl.[7] .................................................. C12M 1/34

[52] U.S. Cl. .................................. 435/287.2; 435/305.4; 435/91.1; 422/102; 215/316

[58] Field of Search .................................. 220/255, 256; 215/273, 279, 280, 282, 287, 288, 315, 316, 287.2; 435/289.1, 303.2, 304.1, 305.3, 305.4, 91.1; 422/102

[56] References Cited

U.S. PATENT DOCUMENTS

| | | | |
|---|---|---|---|
| 5,443,791 | 8/1995 | Cathcart et al. | 422/65 |
| 5,656,493 | 8/1997 | Mullis et al. | 435/286.1 |
| 5,989,499 | 11/1999 | Catanzariti et al. | 422/63 |

*Primary Examiner*—David A. Redding
*Attorney, Agent, or Firm*—Rankin, Hill, Porter & Clark LLP

[57] ABSTRACT

The invention relates to a thermocycler apparatus for implementing chemical and/or biological reactions and a method for activating the thermocycler apparatus. The thermocycler apparatus in accordance with the invention comprises a basebody in which for accommodating one or more reaction vessels open at the top an accommodating portion is configured. For closing off the accommodating portion of the basebody a cover is provided. Spring elements are arranged on the thermocycler apparatus such that the cover and the reaction vessel(s) are urged together and the reaction vessels are closed off directly by the cover or by means of an interlayer.

The invention is characterized by an electrochemical linear motor arranged such that the cover and the reaction vessel(s) are urged together by a pressure higher than that produced by the spring.

Providing the linear motor enables the additional compressive force to be exerted independently of the closing action of the cover and permits the compressive force to be freely varied and precisely defined.

23 Claims, 1 Drawing Sheet

THERMOCYCLER APPARATUS

Figure 1:
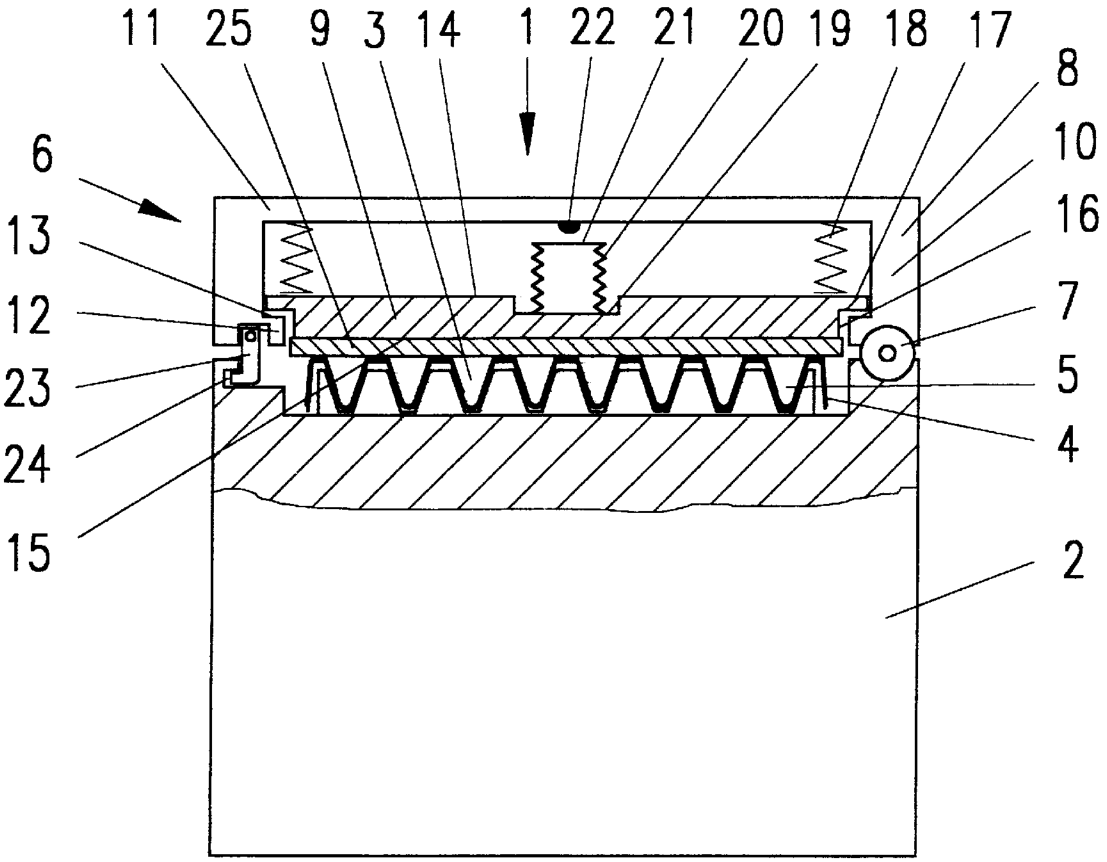

The invention relates to a thermocycler apparatus for implementing chemical and/or biological reactions including a basebody in which for accommodating one or more reaction vessels open at the top an accommodating portion is configured, a cover for closing off the accommodating portion of the basebody, a spring element arranged such that the cover and the reaction vessel(s) are urged together and the reaction vessels are closed off directly by the cover or by means of an interlayer.

Such thermocycler apparatuses are known. They are used as stand-alone devices or are also integrated in automated systems to implement one or more, more particularly molecular-biological reactions fully or semi-automatically. One such automated system including an integrated thermocycler apparatus is disclosed e.g. by U.S. Pat. No. 5,443,791. One application typical of thermocyclers is the PCR method. An apparatus for implementing the PCR method reads from U.S. Pat. No. 5,656,493.

The spring element of the thermocycler apparatus as cited at the outset serves the pressure closure of reaction vessels during implementation of a chemical and/or biological reaction so that the reagents and vapors contained therein cannot escape. More particularly, the intention is to safeguard against cross-contamination of the reagents of a reaction vessel by those of a neighboring reaction vessel. This is why a powerful spring element is made use of to achieve a hermetic seal, this spring element exerting with the cover closed a compressive force of approx. 200 N on the reaction vessels or on a layer of rubber. This high force needs to be exerted when closing the cover. When the thermocycler apparatus is used as a stand-alone device it is closed as a rule by hand, this requiring the operator to apply a strong force. It is for this reason that the cover is provided with a long protruding lever so that it is easier to close by the operator. However, even though closing is facilitated by this lever, there is a risk on opening that the cover is jolted open by the high spring tension and spillage of the complete thermocycler apparatus occurring, as a result of which the contents of one reaction vessel may be caused to slosh over into a neighboring reaction vessel, thus constituting an additional risk of cross-contamination.

To get round this problem a thermocycler apparatus has been developed in which the cover is configured two-part of a cover basebody and a cover segment movably arranged in the cover basebody. Arranged between the cover segment and the cover basebody is a mechanical tensioning means including a mechanical friction clutch by means of which an additional force is exerted on the cover segment with the cover closed, the cover segment being urged against the reaction vessels arranged as a rule in a pipetting plate. Although this tensioning mechanism substantially solves the problems in opening and closing, only a single specific pressure can be set with the tensioning mechanism, however. When differing pipetting plates are used, this pressure should be adjustable individually, since pipetting plates having only a few reaction vessels require less pressure than pipetting plates having a lot of reaction vessels.

In addition to this such an embodiment including a mechanical friction clutch is not suitable for an automated application since automated operation of a mechanical friction clutch is not possible at reasonable expense.

The invention is based on the object of sophisticating a thermocycler apparatus as set forth in the preamble of claim 1 that is simple to handle, that enables an individually adjustable pressure to be exerted on one or more reaction vessels accommodated in the thermocycler apparatus and that features a simple configuration.

This object of the invention is achieved by a thermocycler apparatus having the features as set forth in claim 1. Advantageous aspects of the invention read from the subclaims.

The thermocycler apparatus in accordance with the invention for implementing chemical and/or biological reactions comprises a basebody in which for accommodating one or more reaction vessels open at the top an accommodating portion is configured, and a cover for closing off the accommodating portion of the basebody. A spring element is arranged in the thermocycler apparatus such that the cover and the reaction vessel(s) are urged together and the reaction vessels are closed off directly by the cover or by means of an interlayer. The thermocycler apparatus in accordance with the invention is characterized by an electrically activatable positioner arranged such that the cover and the reaction vessel(s) are urged together by a pressure higher than a pressure produced by the spring.

Providing an electrically activatable positioner, more particularly an electrochemical linear motor enables the necessary compressive force to be applied independently of the closing action of the thermocycler apparatus.

When providing an electrochemical linear motor as the electrically activatable positioner the compressive force can be varied by applying a corresponding current or by discharging the electrochemical linear motor via an electrical resistor. Providing the electrochemical linear motor permits in addition a very simple configuration of the thermocycler apparatus in accordance with the invention, whereby despite the wide range for adjusting the pressure no complicated mechanical elements such as e.g. clutches, gears and the like are needed.

Such electrochemical linear motors are described e.g. in the 1998 Issue No. 105 of the German microsystems journal "F & M, Feinwerktechnik, Mikrotechnik, Mikroelektronik, Zeitschrift FŸr Elektronik, Optik and Mikrosystemtechnik" on pages 527–530, in German patents DE 43 31 764 C1, DE 43 31 763 C1, DE 41 16 739 C1 and in DE 33 16 258 C2.

The electrochemical linear motor may be arranged in both the cover and basebody of the thermocycler apparatus in accordance with the invention; the important thing being that actuation of the linear motor results in a compressive force being exerted on the intermediate surface area or interlayer between the reaction vessel(s) and the cover.

In one preferred embodiment of the thermocycler apparatus in accordance with the invention the linear motor is secured only by one end to part of the thermocycler apparatus, the other end being freely movable, a switch being provided such that contact between the freely movable end of the linear motor and the part located opposite thereto can be sensed, Such an arrangement enables the use of pipetting plates differing in thickness, since these differences can be compensated by the linear motor. At the same time by detecting a mechanical contact between the freely movable end of the linear motor and the part of the thermocycler apparatus located opposite thereto the control for generating a predetermined force is started.

The invention will now be detained with reference to the sole drawing illustrating an example embodiment in a partly sectioned side view schematically.

The thermocycler apparatus 1 shown in the drawing for implementing chemical and/or biological reactions, such as e.g. the PCR method, comprises a housing 2 serving as the basebody which is configured cubical. The upper defining surface area of the housing 2 is configured as the portion 3 accommodating a pipetting plate 4. The pipetting plate 4 is a thin-walled plastics part in which several reaction vessels 5 are molded arranged in rows and columns in the pipetting plate. Typically the pipetting plate comprises 24, 48 or 96 reaction vessels, although pipetting plates exist having larger or smaller reaction vessels which may be put to use as required. Accordingly the height of the individual pipetting plates may also differ. The accommodating portion 3 is provided with blind holes open at the top into which the corresponding reaction vessels 5 of the pipetting plate 4 are inserted. The reaction vessels are preferably located positively connecting the blind holes to achieve a good heat transfer.

A heating and/or cooling element, such as e.g. a Peltier element may be provided at the accommodating portion 3 for heating and cooling the reaction vessels 5 of the pipetting plate 4. The remaining portion of the housing 2 arranged below the accommodating portion 3 is provided for accommodating a power supply of an electrical control means and the like by known ways and means. Arranged above the accommodating portion 3 is a cover 6 pivotally secured to the housing 2 by a hinge joint 7. Preferably a motor for pivoting the cover about the hinge joint is provided, such a motor permitting fully automatic opening and closing of the cover.

The cover is configured as a cover basebody 8 and a cover segment 9, the cover basebody 8 being a hollow cubical body having four sidewalls 10 and a top wall 11. Configured at the lower edge of the sidewalls 10 is an inwardly protruding circumferential ledge 12 forming by its upper defining surface area 13 a stop 12 for the cover segment 9. The cover segment 9 forms preferably a heating plate which is heatable to a temperature slightly above the maximum reaction temperature generated by the heating and/or cooling element arranged in the accommodating portion 3. The heating and/or cooling element may, for example, cover a temperature profile in the range 0C to 95° C., the cover segment 9 then being heated to, for example, 100° C., thus preventing condensation at the cover segment.

The cover segment 9 is a substantially flat plate having a top side 14 and an underside 15 and a narrow edging surface area 16 on all sides. Protruding from the upper edge of the edging surface area 16 is a ledge 17 on all sides of the cover segment 9, this ledge forming by its lower defining surface area a counterstop 17 to the stop 12 of the cover basebody 8. The cover segment 9 is thus arranged shiftable along its axes normal to the cover basebody 8. Arranged between the top side 14 of the cover segment 9 and the top wall 11 are spring elements 18 which urge the cover segment 9 against the stop 13 of the cover basebody 8. The spring elements 18 are helical springs, preferably four such spring elements 18 being arranged in the comer portions of the cover segment 9. These spring elements 18 are pretensioned for example with a spring force totalling approx. 20 N.

Incorporated in the middle portion of the top side 14 of the cover segment 9 is a dish 19 in which an electrochemical linear motor 20 is arranged. Such electrochemical linear motors, also termed electrochemical actors, are described e.g. in the 1998 Issue No. 105 of the German microsystems journal "F & M, Feinwerktechnik, Mikrotechnik, Mikroelektronik, Zeitschrift fŸr Elektronik, Optik and Mikrosystemtechnik on pages 527–530 and available from the Company FRIWO Silberkaft Gesellschaft fŸr Batterietechnik mbH, Meiderichterstr. 6-8, D-47058 Duisburg under Article Order No. 5/300-AF. This electrochemical linear motor comprises a hermetically sealed bellows-type housing provided with two electrical input leads so that in the bellows-type housing e.g. the following reversible electrochemical reactions can be sequenced controlled $$Ni(OH)_2 <-> NiO(OH) + \tfrac{1}{2}H_2.$$

On application of current, i.e. in charging the electrochemical motor, hydrogen is liberated in the bellows as a result of which the bellows is extended, producing a linear movement. When the power supply is interrupted the bellows remains in this position. When the bellows is discharged via an electrical resistor the hydrogen gas recombines chemically resulting in the gas volume being reduced and the bellows contracted. In its mechanical response the electrochemical linear motor corresponds to a pneumatic element which requires no external supply of compressed air, however, but is instead electrically activatable in three controlled conditions, namely charging, holding and discharging.

The electrochemical linear motor 20 is secured by one end in the cavity 19 of the cover segment 9 whilst its opposite end 21 is freely movable. When the electrochemical linear motor is actuated, i.e. in extending the bellows, the electrochemical linear motor 20 is supported by the top wall 11 of the cover basebody 8 it thereby urging the cover segment 9 away from the top wall 11, i.e. downwards in the direction of the accommodating portion 3 of the housing 2 when the thermocycler apparatus is closed.

The thermocycler apparatus 1 in accordance with the invention comprises preferably at the top wall 11 of the cover basebody 8 at the portion opposite the freely movable end 21 of the linear motor 20 a switch 22 with which a contact of the freely movable end 21 with the top wall 11 of the cover basebody 8 can be sensed and converted into a electrical signal. The switch 22 is, for example, a microswitch.

The switch 22 is connected to an electrical control means activating the linear motor 20.

Provided at the side of the cover 6 opposite the hinge joint 7 is a locking element 23 capable of engaging a corresponding locking cavity 24 in the housing 2 and locking the cover 6 in place on the housing 2.

In the example embodiment as shown in the drawing a rubber mat 25 is loosely arranged between the cover segment 9 and the pipetting plate 4. This rubber mat 25 may be replaced together with the corresponding pipetting plate 4 or cleaned between two incubation procedures. However, it is also possible to operate the thermocycler apparatus in accordance with the invention without such a rubber mat or to apply such a layer of rubber durably to the underside of the cover segment 9.

The functioning of the thermocycler apparatus in accordance with the invention will now be described.

With the cover 6 open a pipetting plate 4 is inserted in the accommodating portion 3. The cover 6 is hinged down onto the housing 2 by means of the hinge joint 7 until the locking element 23 engages the locking cavity 24 and the cover is locked in place on the housing 2. In this arrangement the electrochemical linear motor 20 is in its contracted condition so that the cover segment 9 is urged against the rubber mat 25 downwards in the direction of the accommodating portion 3 solely by the effect of the spring elements 18. In the closing movement only the relatively small tensioning force of the spring element 18 needs to be overcome, corresponding to a preload of e.g. 20 N.

Once the cover 6 is locked in place on the housing 2 by the locking mechanism 23, 24 the linear motor 20 is actuated, i.e. the linear motor is powered so that it extends. The control means detects by means of the microswitch 22 the point in time $t_{contact}$ at which the linear motor 20 comes into contact by its freely movable end 21 with the top wall 11 of the cover basebody 8. As of this point in time of contact the linear motor 20 is supplied a specific electrical charge dictated by the product (I·t) of the current I and time t which is proportional to the force exerted by the linear motor 20 so that the force with which the linear motor 20, in addition to that of the spring element 18, urges the cover segment 9 in the direction of the accommodating portion 3 can be precisely defined. The force exerted by the electrochemical linear motor 20 is typically of the order of approx. 200 N and may amount preferably to as high as 300 N. For the invention, linear motors having a maximum force of 150 N to 800 N are expedient.

The force exerted by the linear motor 20 is optionally variable by varying the charge supplied. This force is thus optionally adaptable to individual requirements, it being expedient to reduce the force for pipetting plates having few reaction vessels and to increase the force for pipetting plates having many or larger reaction vessels.

By providing the switch 22 the force exerted by the linear motor 20 is independent of the thickness of the rubber mat 25 or the thickness of the pipetting plates 4 since the force is not built up until the freely movable end 21 is in contact with the top wall 11 of the cover and the charge supplied can be precisely defined as of this point in time.

In a simplified embodiment in which the thickness of the interlayer 25 and the pipetting plate 4 is the same in each case or in which no interlayer 25 is provided at all, the switch 22 may also be omitted, since then the spacing between the top wall 11 and the freely movable end 21 of the linear motor 20 when fully retracted is always the same and thus the electrical charge to be supplied to the linear motor 20 until the freely movable end 21 comes into contact with the top wall 11 is likewise always the same. In such a simplified embodiment the force exerted by the linear motor 20 is proportional to the total electrical charge supplied to the linear motor 20 less the necessary but constant electrical charge up to contact being made between the linear motor 20 and the top wall.

In a modified embodiment the switch 22 is arranged at the cover segment 9 and the electrochemical linear motor 20 secured to the top wall 11. The switch 22 may be configured as an electrically conducting, for example, annular contact field, the housing of the electrochemical linear motor 20 functioning as the companion contact. The corresponding control current circuit is thus circuited via the housing of the linear motor, commencement of the force being built up being sensed when contact is made between the housing of the linear motor and the contact field.

In another modified embodiment a rubber bellows is arranged surrounding the electrochemical linear motor so that a narrow cavity between the housing of the linear motor and the rubber bellows is formed. Furthermore, a fan is provided to blow cooling air for cooling the linear motor in this cavity, thus enabling the useful life of the linear motor to be prolonged.

When use is made of a linear motor having a defined stroke, it may prove expedient to arrange a shim on the cover segment 9. In this arrangement shims differing in thickness are interchangeable so that the stroke can be adapted to microtitration plates differing in thickness. Preferably the shims are securable by a quick-release fastener to the cover segment 9.

It is also expedient to configure the locking mechanism 23, 24 electrically activatable to thus prevent unauthorized opening of the cover whilst it is still tensioned by the linear motor.

The thermocycler apparatus in accordance with the invention comprises in the basebody 2 a main heating means and a control means with a further heating means in the cover 6. During operation the cover heating means is maintained at a value as set by the user to prevent condensation, this value being, for example, in the range 70° C. to 120° C. Preferably the cover heating means having a much slower response than the main heating means is simultaneously started on actuation of the linear motor 10. The main heating means commences its heating cycle when the cover heating means has either attained its set final temperature or has exceeded a threshold value.

It is understood that the invention is not restricted to the example embodiments as described above, it also being possible—without departing from the scope of the invention—to configure the housing two-part with a housing basebody and a housing segment on which the accommodating portion for reaction vessels is configured. Between the housing segment and the housing basebody the spring elements and the electrochemical linear motor may then be arranged to urge the accommodating portion upwards in the direction of the cover. For the invention it is essential that the majority of the compressive force needs to be applied between the reaction vessels and the cover not in the locking action of the cover but is generated by the linear motor after the cover has been locked and released prior to the cover being opened. It is due to this arrangement that the cover can be handled just as easily as with conventional thermocycler apparatuss but now with substantially less compressive force between the reaction vessels and the cover. Jolting open of the cover due to its considerable preloading is reliably prevented by the configuration in accordance with the invention. At the same time the compressive force can now be freely varied and precisely defined over a wide range. These advantages are achieved with high cost-effectiveness and simple design.

Due to its simplicity the example embodiment as described above is a particularly preferred embodiment of the invention. However, it also being possible—without departing from the scope of the invention—to provide another electrically activatable positioner with which the desired pressure can be generated automatically. One such positioner may be, for example, a toggle joint powered either by an electric motor and spindle or by a cam or wedge-type mechanism powered by electric motor.

List of Reference Numerals 1. thermocycler apparatus
2. housing
3. accommodating portion
4. pipetting plate
5. reaction vessel
6. cover
7. hingejoint
8. cover basebody
9. cover segment
10. switch
11. top wall
12. ledge
13. upper defining surface area/stop
14. top side
15. underside
16. edging surface area
17. counterstop 18. spring element
19. cavity
20. electrochemical linear motor
21. freely movable end
22. switch
23. locking element
24. locking cavity
5. rubber mat

What is claimed is:

1. A thermocycler apparatus for implementing chemical and/or biological reactions including:

a basebody in which for accommodating one or more reaction vessels open at the top an accommodating portion is configured, a cover for closing off said accommodating portion of said basebody, a locking mechanism for locking said cover in place on said basebody wherein an electrically activatable positioner is arranged such that after said cover has been locked in place on said basebody said cover and said reaction vessel(s) can be urged together.

2. The thermocycler apparatus as set forth in claim 1 wherein said electrically activatable positioner is an electrochemical linear motor.

3. The thermocycler apparatus as set forth in claim 2 wherein a spring element arranged such that said cover and said reaction vessel(s) are urged together and said reaction vessels are closed off directly by said cover or by means of an interlayer, said linear motor permitting exertion of a pressure higher than the pressure produced by said spring element.

4. The thermocycler apparatus as set forth in claim 3 wherein said cover is formed by a cover basebody and a cover segment, and said spring element and said linear motor are arranged between said cover basebody and said cover segment.

5. The thermocycler apparatus as set forth in claim 3 wherein said basebody is formed by a basebody and a base segment and said spring element and said linear motor are arranged between said basebody and said base segment.

6. The thermocycler apparatus as set forth in claim 5 wherein said electrochemical linear motor is an electrochemical actor generating a translational movement by electrochemical conversion of a reversible chemical reaction.

7. The thermocycler apparatus as set forth in claim 6 wherein said electrochemical linear motor comprises a hermetically sealed spring bellows in which said reversible chemical reaction is sequenced.

8. The thermocycler apparatus as set forth in claim 1 wherein said electrically activable positioner is configured such that it is capable of exterting a maximum force of 150 N to 800 N and preferably 300 N.

9. The thermocycler apparatus as set forth in claim 7 wherein said electrochemical linear motor is configured such that it is capable of exterting a maximum force of 150 N to 800 N and preferably 300 N.

10. The thermocycler apparatus as set forth in claim 1 comprising a control means exerting a predetermined force by application of a predetermined current for a predetermined time duration on said electrochemical linear motor.

11. The thermocycler apparatus as set forth in claim 9 comprising a control means exerting a predetermined force by application of a predetermined current for a predetermined time duration on said electrochemical linear motor.

12. The thermocycler apparatus as set forth in claim 11 wherein said electrochemical linear motor is secured to either said cover segment, to said cover basebody, base segment or to said basebody by one end and the opposite end of said linear motor is freely movable and that a switch is provided such that a contact can be sensed between said freely movable end of said linear motor and said part of said cover or basebody opposite said freely movable end of said linear motor.

13. The thermocycler apparatus as set forth in claim 12 wherein said switch is arranged at said freely movable end of said linear motor.

14. The thermocycler apparatus as set forth in claim 12 wherein said switch is arranged at said part of said cover or basebody opposite said freely movable end of said linear motor.

15. The thermocycler apparatus as set forth in claim 1 wherein said accommodating portion of said basebody is adapted to the contour of a pipetting plate comprising a plurality of reaction vessels.

16. The thermocycler apparatus as set forth in claim 12 wherein said accommodating portion of said basebody is adapted to the contour of a pipetting plate comprising a plurality of reaction vessels.

17. The thermocycler apparatus as set forth in claim 4 wherein a heating and/or cooling element is integrated in said cover segment.

18. The thermocycler apparatus as set forth in claim 16 wherein a heating and/or cooling element is integrated in said cover segment.

19. The thermocycler apparatus as set forth in claim 1 wherein a heating and/or cooling element is integrated in said basebody.

20. The thermocycler apparatus as set forth in claim 18 wherein a heating and/or cooling element is integrated in said basebody.

21. The thermocycler apparatus as set forth in claim 4 wherein said electrochemical linear motor is secured to either said cover segment, to said cover basebody, base segment or to said basebody by one end and the opposite end of said linear motor is freely movable and that a switch is provided such that a contact can be sensed between said freely movable end of said linear motor and said part of said cover or basebody opposite said freely movable end of said linear motor.

22. A method for activating a thermocycler apparatus configured as set forth in the claim 21 comprising the steps actuating said electrochemical linear motor by applying a current prior to commencement of a chemical and/or biological reaction and after locking said cover in place by said locking mechanism, detecting said current by said control means when said switch is switched between said freely movable end of said linear motor and said cover part located opposite thereto, and as of this point in time applying said current for a predetermined time duration to said linear motor to generate a predetermined force.

23. The method as set forth in claim 22 comprising the steps retracting said linear motor on completion of said chemical and/or biological reaction by discharging it via an electrical resistor, to permit opening said cover substantially non-tensioned.

* * * * *